US005593392A

United States Patent [19]

Starchevich

[11] Patent Number: 5,593,392
[45] Date of Patent: Jan. 14, 1997

[54] INTRAVENOUS FLOW REGULATING AND MOUNTING ASSEMBLY

[76] Inventor: Jovanka Starchevich, 138 Sullivan St., New York, N.Y. 10012

[21] Appl. No.: 319,167

[22] Filed: Oct. 6, 1994

Related U.S. Application Data

[63] Continuation-in-part of Ser. No. 186,441, Jan. 25, 1994, Pat. No. 5,429,615, which is a continuation-in-part of Ser. No. 949,148, Sep. 22, 1992, Pat. No. 5,328,487.

[51] Int. Cl.$^6$ .................................................. A61M 5/00
[52] U.S. Cl. .......................... 604/246; 604/250; 604/118; 251/4
[58] Field of Search .................................... 604/246, 247, 604/118, 65, 67, 30, 32, 33, 34, 36, 80, 257, 131, 178, 253, 260, 180, 248, 249, 250, 25, 258; 128/DIG. 6, DIG. 12, DIG. 13; 251/6, 9, 10, 4; 248/74.1, 74.2, 75

[56] References Cited

U.S. PATENT DOCUMENTS

| | | | |
|---|---|---|---|
| 2,366,424 | 1/1945 | Perry | 604/34 X |
| 2,844,351 | 7/1958 | Smith | 604/250 X |
| 3,822,052 | 7/1974 | Lange | 251/10 |
| 3,915,167 | 10/1975 | Waterman | 604/250 |
| 3,942,228 | 3/1976 | Buckman et al. | 251/4 |
| 4,061,142 | 12/1977 | Tuttle | 604/34 |
| 4,170,995 | 10/1979 | Levine et al. | 604/180 |
| 4,247,076 | 1/1981 | Larkin | 251/7 |
| 4,355,638 | 10/1982 | Iwatschenko et al. | 604/65 |
| 4,428,745 | 1/1984 | Williams | 604/6 |
| 4,434,963 | 3/1984 | Russell | 251/7 |
| 4,606,735 | 8/1986 | Wilder et al. | 604/180 |
| 4,634,092 | 1/1987 | Daniell et al. | 251/7 |
| 4,642,093 | 2/1987 | Härle | 604/54 |
| 4,775,360 | 10/1988 | Lane et al. | 604/4 |
| 5,005,793 | 4/1991 | Shillington | 248/229 |
| 5,014,962 | 5/1991 | Adelberg | 251/6 |
| 5,083,741 | 1/1992 | Sancoff | 251/9 |
| 5,203,056 | 4/1993 | Funk et al. | 24/543 |
| 5,203,769 | 4/1993 | Clemont et al. | 604/32 |
| 5,209,441 | 5/1993 | Satoh | 248/74.2 |
| 5,232,193 | 8/1993 | Skakoon | 251/4 |
| 5,238,218 | 8/1993 | Mackal | 251/10 |
| 5,259,587 | 11/1993 | D'Alessio et al. | 251/4 |
| 5,316,246 | 5/1994 | Scott et al. | 248/68.1 |

FOREIGN PATENT DOCUMENTS

0448202  3/1968  Switzerland .......................... 248/74.1

*Primary Examiner*—Corrine M. McDermott
*Assistant Examiner*—V. Alexander
*Attorney, Agent, or Firm*—McAulay Fisher Nissen Goldberg & Kiel, LLP

[57] ABSTRACT

A flow regulator device for intravenous tubing comprises a frame body, a notch on the frame body for attaching an intravenous tube to the frame body, and a first pressure applicator disposed on the frame body and engageable with the intravenous tube for alternately compressing and releasing the intravenous tube in a first direction of action in a first plane. A second pressure applicator is provided on the frame body for alternately compressing and releasing the intravenous tube in a second direction of action in a second plane. The second pressure applicator is disposed on the frame body in spaced relation to the first pressure applicator along a flow path of the intravenous tube and is engageable with the intravenous tube. The second direction of action (of the second pressure applicator) is oriented at a substantial angle with respect to the first direction of action, whereas the plane of action of the second pressure applicator is spaced from the plane of action of the first pressure applicator along the flow path of the intravenous tube. The flow regulator device further comprises an actuator disposed on the frame and operatively connected to the first pressure applicator and the second pressure applicator for operating the pressure applicators to vary a fluid flow cross-section in the intravenous tube.

25 Claims, 8 Drawing Sheets

INTRAVENOUS FLOW REGULATING AND MOUNTING ASSEMBLY

CROSS REFERENCE TO A RELATED APPLICATION

This application is a continuation-in-part U.S. patent application 08/186,441 filed Jan. 25, 1994, now U.S. Pat. No. 5,429,615, which was a continuation-in-part of application Ser. No. 07/949,148 filed Sep. 22, 1992, now U.S. Pat. No. 5,328,487.

BACKGROUND OF THE INVENTION

The invention relates to apparatus for mounting intravenous tubes and for controlling the flow of fluids through intravenous tubes.

Intravenous tubes have been widely used for supplying nutrients and medication to patients. In many cases the same patient may have more than one such tube connected to his or her body. In some cases several tubes may be connected to each of several patients that are located in adjacent beds. In emergency situations it is of great importance to be able to quickly determine with absolute certainty which tube is connected to which patient and which nutrient or medication.

At least some of the prior art devices are extremely difficult to use. More specifically, at least one uses the combination of an inclined plane and a roller that is moved along the inclined plane to allow more or less flow through the intravenous tube. The so-called Adelberg clamp is delivered pre-assembled to the tube by the manufacturer or are delivered by the manufacturer as a set. Other devices are designed such that it is essential to have access to a free end of the intravenous tube because the clamp can only be slipped on the free end.

OBJECTS OF THE INVENTION

An object of the invention is to provide an improved intravenous flow regulating and mounting apparatus.

A further object of the present invention is to provide such an apparatus which serves to prevent or reduce accidental shutoff, accidental release, or other changes resulting, for example, from pulling on an intravenous tube.

Another object of the invention is to provide such apparatus that will enable the health care professional to alternatively completely shut off flow or to modulate the flow to allow a selection of a desired flow rate.

It is still another object of the invention to provide apparatus which is inexpensive to manufacture.

It is also an object of the invention to provide apparatus that will work with any of various standard size intravenous tubing sizes.

These and other objects of the present invention will be apparent from the drawings and detailed descriptions herein.

SUMMARY OF THE INVENTION

A flow regulator device for intravenous tubing comprises, in accordance with the present invention, a frame body provided with an elongate surface, a slider member, and mounting componentry for slidably mounting the slider member to the frame body for motion along an essentially linear path. The elongate surface extends along the linear path and is inclined relative thereto, while the slider member has a pressure surface juxtaposed directly to the elongate surface so that an intravenous tube is insertable between the elongate surface and the pressure surface in direct contact with the elongate surface and the pressure surface. Accordingly, motion of the slider member along the elongate surface changes a distance between the pressure surface and the elongate surface to thereby vary a fluid flow cross-section in the intravenous tube inserted between the pressure surface and the elongate surface.

According to a further feature of the present invention, the mounting componentry includes at least one guide rail rigid with the frame body and an additional rail movably connected to the frame body. The elongate surface extends along the rail, while the slider member is in slidable contact with the additional rail for moving the additional rail alternatively towards and away from the guide rail to alternately compress and release the intravenous tube. More specifically, the additional rail moves in a first plane in response to sliding of the slider member along the guide rail, the elongate surface being inclined in a second plane oriented at a substantial angle with respect to the first plane. That angle may be approximately 90 degrees.

According to an even more specific feature of the present invention, the guide rail and the additional rail are legs of a U-shaped clamping member incorporated into the frame body.

According to another feature of the present invention, the flow regulator device further comprises a holder on the frame body for maintaining the intravenous tube in a predetermined position between the pressure surface and the elongate surface. The holder may include a notch in the frame body for receiving the intravenous tube.

A flow regulator device for intravenous tubing comprises, in accordance with another embodiment of the present invention, (i) a frame body, (ii) at least one attachment element on the frame body for attaching an intravenous tube to the frame body, (iii) a first pressure applicator disposed on the frame body and engageable with the intravenous tube for alternately compressing and releasing the intravenous tube in a first direction of action in a first plane, and (iv) a second pressure applicator for alternately compressing and releasing the intravenous tube in a second direction of action in a second plane. The second pressure applicator is disposed on the frame body in spaced relation to the first pressure applicator along a flow path of the intravenous tube and is engageable with the intravenous tube. The second direction of action (of the second pressure applicator) is oriented at a substantial angle with respect to the first direction of action, whereas the plane of action of the second pressure applicator is spaced from the plane of action of the first pressure applicator along the flow path of the intravenous tube. The flow regulator device further comprises an actuator disposed on the frame and operatively connected to the first pressure applicator and the second pressure applicator for operating the pressure applicators to vary a fluid flow cross-section in the intravenous tube.

In accordance with another feature of the present invention, the first pressure applicator includes a first clamping surface and a second clamping surface movable relative to another, the first clamping surface and the second clamping sur- face extending at all times in substantially parallel planes. The second pressure applicator likewise includes a third clamping surface and a fourth clamping surface movable relative to one another, the third clamping surface and the fourth clamping surface being disposed at all times in substantially parallel planes. The planes of the first clamping surface and the second clamping surface are oriented at the angle relative to the planes of the third clamping surface and the fourth clamping surface. The first clamping surface and the second clamping surface define therebetween a first gap, while the third clamping surface and the fourth clamping surface define a second gap. The gaps are substantially aligned with one another so that the intravenous tube is insertable in the first gap between the first clamping surface and the second clamping surface and in the second gap between the third clamping surface and the fourth clamping surface. The actuator includes a shifting mechanism mounted to the frame body for shifting the first clamping surface and the second clamping surface alternately towards and away from one another and for shifting the third clamping surface and the fourth clamping surface alternately towards and away from one another to thereby vary a fluid flow cross-section in an intravenous tube inserted in the first gap between the first clamping surface and the second clamping surface and in the second gap between the third clamping surface and the fourth clamping surface.

The first clamping surface and the third clamping surface may be stationary with respect to the frame body, while the second clamping surface and the fourth clamping surface are attached to a carrier member movably mounted to the frame body. In that event the shifting mechanism is operatively connected to the carrier member to shift the carrier member alternatively in opposite directions.

In a specific embodiment of the present invention, the shifting mechanism includes a slider member and a spring biased element with a camming surface engaging the slider member. The spring biased element may be a leg of a U-shaped clamping member incorporated into the frame body.

In an alternative specific embodiment of the present invention, the shifting means includes a screw mechanism.

In accordance with another feature of the present invention, the planes of the first clamping surface and the second clamping surface and the planes of the third clamping surface and the fourth clamping surface are oriented at an acute angle relative to the direction of reciprocative motion of the carrier member.

In accordance with a further feature of the present invention, the actuator includes means for simultaneously operating the first pressure applicator and the second pressure applicator to vary a fluid flow cross-section in the intravenous tube.

A flow regulator device for intravenous tubing comprises, in accordance with another conceptualization of the present invention, a frame body, an attachment element on the frame body for attaching an intravenous tube to the frame body, and a pressure applicator disposed on the frame body and engageable with the intravenous tube for compressing and simultaneously twisting the intravenous tube to vary a fluid flow cross-section in the intravenous tube. As set forth above, the pressure applicator may include a first pressure applicator disposed on the frame body and engageable with the intravenous tube for alternately compressing and releasing the intravenous tube in a first direction of action in a first plane and further include a second pressure applicator, disposed on the frame body spaced from the first pressure applicator along a flow path of the intravenous tube and engageable with the intravenous tube, for alternately compressing and releasing the intravenous tube in a second direction of action in a second plane. The second direction of action is oriented at a substantial angle with respect to the first direction, while the second plane is spaced from the first plane along the flow path of the intravenous tube. An actuator means is on the frame and is operatively connected to the first pressure applicator and the second pressure applicator for operating the pressure applicators to vary a fluid flow cross-section in the intravenous tube.

A method for use in intravenous feeding comprises, in accordance with the present invention, the steps of attaching an intravenous tube to a frame body or a flow regulating device and, upon attachment of the intravenous tube to the frame body, operating pressure application componentry on the frame body to compress the intravenous tube in a first direction of action in a first plane and simultaneously compress the intravenous tube in a second direction of action in a second plane to thereby vary a fluid flow cross-section in the intravenous tube. The second direction of action is oriented at a substantial angle with respect to the first direction and the second plane is spaced from the first plane along a flow path of the intravenous tube, whereby the intravenous tube is twisted during the steps of compressing.

Pursuant to another feature of the present invention, the step of operating the pressure application componentry includes the step of moving a first clamping surface and a second clamping surface relatively towards one another along the first direction and further includes the step of moving a third clamping surface and a fourth clamping surface relatively towards one another along the second direction. Preferably, during the step of moving the clamping surfaces, the first clamping surface and the second clamping surface are maintained substantially parallel to one another and the third clamping surface and the fourth clamping surface are also maintained substantially parallel to one another.

Pursuant to a further feature of the present invention, the first clamping surface and the second clamping surface define therebetween a first gap and the third clamping surface and the fourth clamping surface define therebetween a second gap substantially aligned with respect to the first gap. The step of attaching the intravenous tube includes the step of inserting the intravenous tube into the first gap and the second gap.

Pursuant to an additional feature of the present invention, the first clamping surface and the second clamping surface are fixed relative to the frame body, the second clamping surface and the fourth clamping surface being formed on a spring biased element movable relative to the frame body. The step of moving the clamping surfaces relative to one another includes the step of sliding a slider member along the spring biased element to push the spring biased element towards the first clamping surface and the third clamping surface.

Where the first clamping surface and the second clamping surface are fixed relative to the frame body, while the second clamping surface and the fourth clamping surface are formed on a carrier member, the step of moving the clamping surfaces relative to one another includes the step of operating a screw mechanism operatively coupled to the spring element.

BRIEF DESCRIPTION OF THE DRAWING

The invention will be better understood by reference to the accompanying drawing in which.

DETAILED DESCRIPTION

Figure 1:
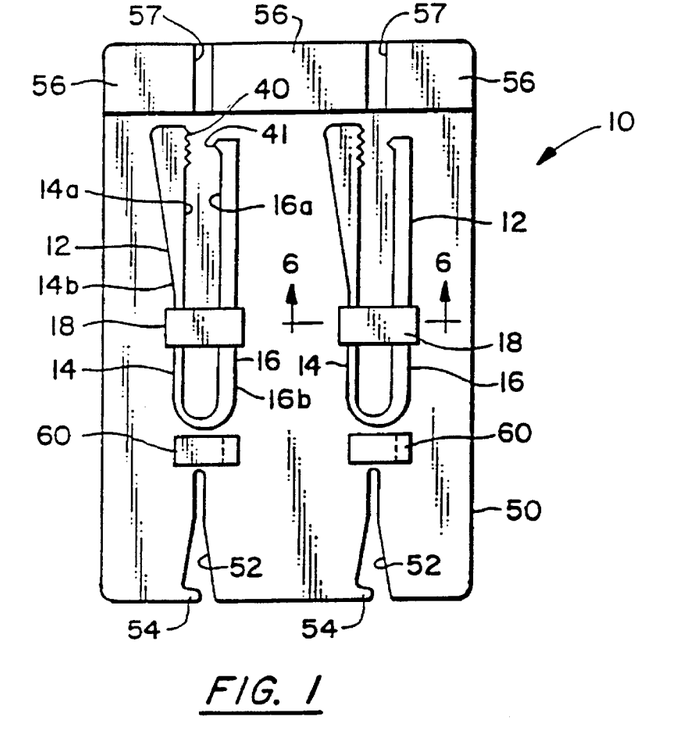
FIG. 1 is a plan view of an intravenous clamping and flow regulating device.
Figure 7:
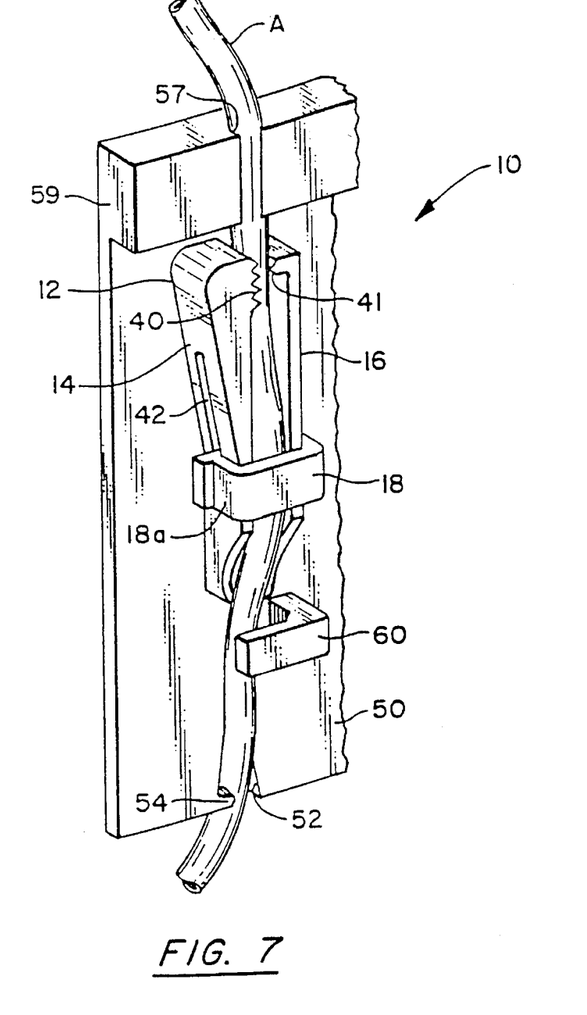
FIG. 7 is a fragmentary perspective view of a portion of the device of FIG. 1.

As illustrated in FIG. 1, a device 10 for engaging at least one associated intravenous tube A used in the delivery of medication or nutrient(s) to a patient includes a first generally U-shaped member 12 having first and second generally straight elongated legs or rails 14, 16. Each of the legs or rails 14, 16 have inner faces 14a and outer faces 14b. The inner faces 14a, 16a are disposed in opposed relation. The first leg 14 is movable, in opposition to an internal spring bias, between a first position in which the respective inner faces 14a, 16a of the first and second legs 14, 16 are disposed in spaced relation and a second position in which the respective inner faces 14a, 16a of the first and second legs 14, 16 are closer than in the first position. The inner faces 14a, 16a are disposed in the first position, illustrated in FIG. 1, with a space therebetween that is sufficient to allow insertion of an associated intravenous tube A. In the second position, illustrated in FIG. 7, the tube A is squeezed to shut off or modulate the flow through the intravenous tubing.

The device further includes a second generally U-shaped member 18 having first and second sides 18a, 18b, respectively engage the outer faces 14b, 16b of the first and second legs 14, 16 of the first generally U-shaped member 12. The second generally U-shaped member 18 may be slidable along a portion of the axial extent of the first and second legs 12, 14. As will be apparent from FIG. 6B this slider member 18 may be pivoted sufficiently to permit installation of the tube A by merely slipping an axial section under the member 18 and within the legs of the member 12. In other words it is not necessary to "thread" the end of the tube into device 10 as is the case with some prior art apparatus.

Figure 6A:
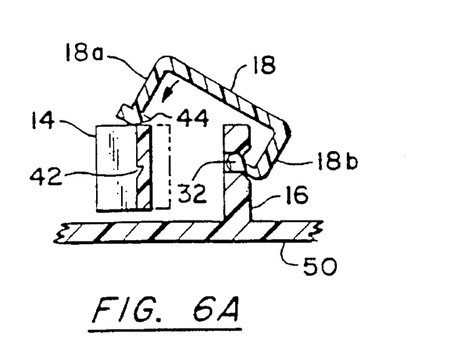
FIG. 6A is a fragmentary sectional view taken along the line 6—6 of FIG. 1.
Figure 6B:
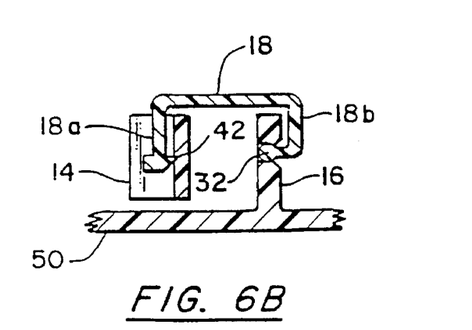
FIG. 6B is a view similar to the view of FIG. 6A showing an alternate position of the slider.
Figure 8:
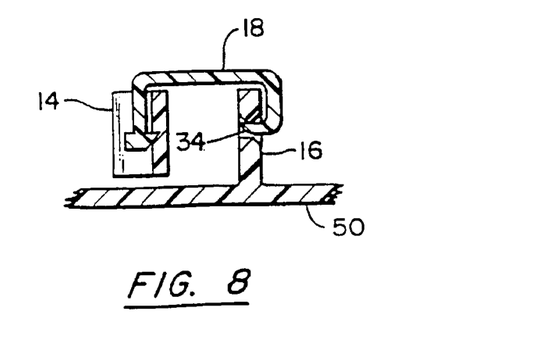
FIG. 8 is a view similar to that of FIG. 6A illustrating an alternative structure.
Figure 9:
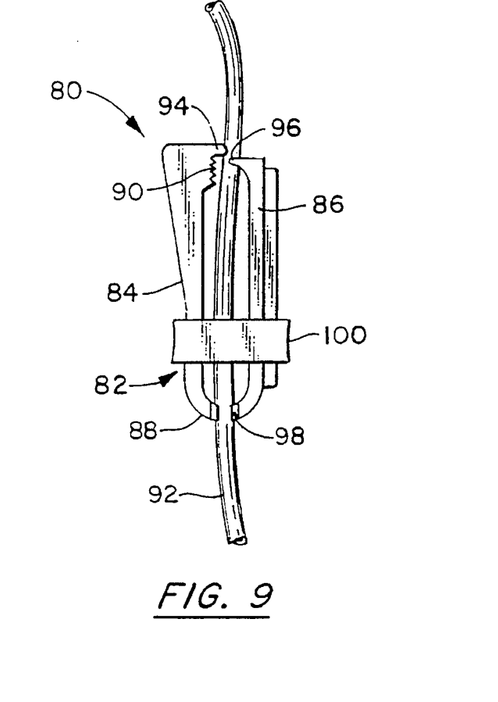
FIG. 9 is a schematic side elevational view of another intravenous clamping and flow regulating device.

Preferably, the apparatus 20 includes means for engaging one of the legs of the first U-shaped member 8. The means for engaging, in the preferred embodiment, includes an elongated slot 30 in the outer face 16b of the leg 16 of the first U-shaped member 12. In the preferred embodiment the means for engaging include an either cylindrical section shaped axial extremity 32 (as shown in FIGS. 6A and 6B) or a hook shaped axial extremity 34 (as shown in FIG. 8) which slide in and engage respectively with either a cylindrical shaped section shaped slot 30 or a rail shaped edge of the slot 30.

The first and second legs 14, 16 of the first generally U-shaped member 12 each have jaws on the inner faces 14a, 16a thereof that are disposed in opposed relationship and that are dimensioned and configured to squeeze the associated intravenous tube in the second position. More specifically, the first leg may be provided with a plurality of laterally extending teeth 40 on the inner face of 14a thereof. The inner face 16 has a single laterally extending ridge shaped surface 41 intended to concentrate forces against the intravenous tube A to either modulate or shut off fluid flow in the tube A. A groove 42 in the outer wall 14b is elongated and engages detent 44 on the outer face 14b of the leg 14.

In the preferred embodiment device 10 includes a generally planar base or frame body 50 that carries the first generally U-shaped member as best seen in FIGS. 1–3, 6A, and 6B. The base 50 includes a V-shaped slot 52 dimensioned and configured to permit insertion therein of the associated intravenous tube A in a manner to shut off fluid flow in the intravenous tube A.

Device 10 may further include means for partially blocking intravenous tube A access to the V-shaped slot 52. The means for blocking is disposed proximate to the open end of the V-shaped slot and is preferably a laterally extending member 54 that partially blocks access to the V-shaped slot 52. This ensures that the tube A does not accidentally fall into the V-shaped slot and thus inadvertently get shut off.

The geometric axis of the V-shaped slot 52 and the first generally U-shaped member are aligned and the apparatus may further include surface 56 for the placement of identifying indicia proximate to the first U-shaped member 12. The apparatus preferably includes a generally L-shaped member 60 extending form the base. The L-shaped member 60 is preferably dimensioned and configured to retain the associated intravenous tube A in the first U-shaped member and is disposed intermediate to the first U-shaped member 12 and the V-shaped slot 52. A slot 57 is preferably disposed in a step shaped part 59 of the base 50 in aligned relation to the geometric axes of the V-shaped slot and the first U-shaped member 12. In various forms of the invention slot 57 may be cylindrical section shaped (not shown) or alternatively have opposed flat mutually parallel walls (not shown). The positive retention of the tube A in the slot 57 is important even if the member 12 is not engaging the tube A. More specifically, the positive location of the tube A is essential to the proper identification of respective tubes and thus the avoidance of errors as the result of confusing the tubes.

It will be seen that the slot 57 is a means for securing the associated intravenous tubing A to the base 50 and the slot 57 is disposed further from the V-shaped slot 52 that form the first U-shaped member 12.

In some forms of the invention, the base 50 is provided with a mounting surface 70 which in the preferred embodiment cooperates with a band (not shown) that typically will extend around the pole (not shown) which supports the intravenous fluid containers (not shown). Various other mounting means will be apparent to those skilled in the art.

It will be seen that the device in accordance with the invention allows the user to modulate the flow through the tube A by sliding the second U-shaped member along legs 14, 16 to cause the desired flow modulation or shutoff. The V-shaped slot is intended as a secondary shutoff means to absolutely insure no inadvertent fluid flow in the tube A.

A major advantage of the device in accordance with the invention is that the user may easily slip the tube A into the first U-shaped member 12. The ease of insertion will be apparent to those skilled in the field.

Figure 2:
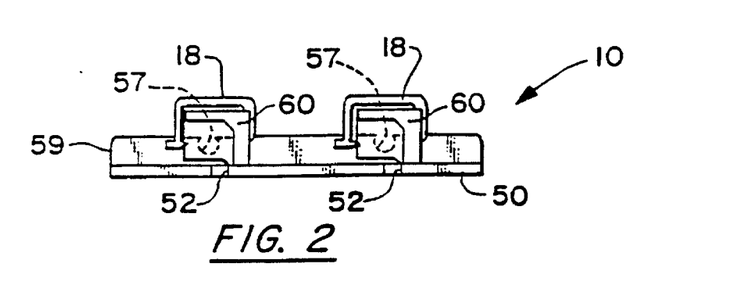
FIG. 2 is front elevational view of the device shown in FIG. 1.
Figure 3:
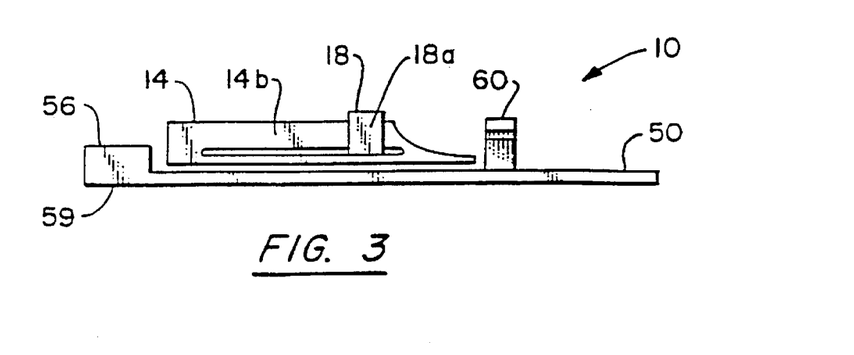
FIG. 3 is left elevational view of the device shown in FIG. 1.
Figure 4:
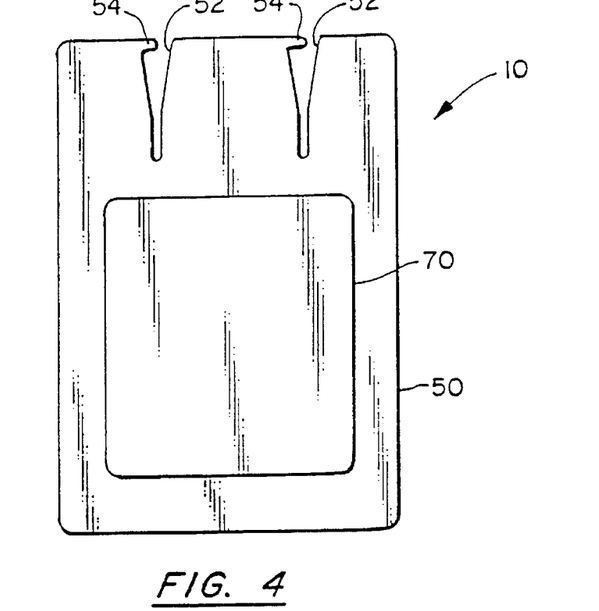
FIG. 4 is a bottom view of the device shown in FIG. 1.
Figure 5:
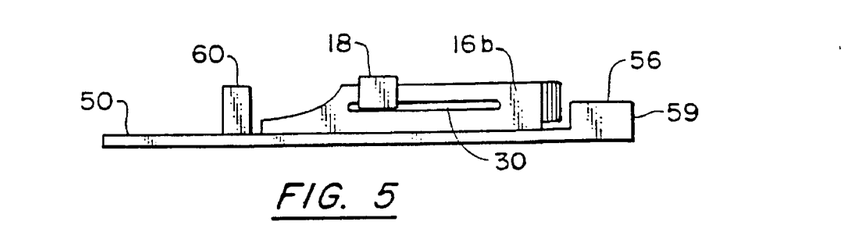
FIG. 5 is right elevational view of the device shown in FIG. 1.

For purposes of simplicity, FIGS. 1 and 2 show only two U-shaped clamping members 12. It will be apparent, however, that a larger number may be provided. Such an arrangement facilitates the orderly placement of the intravenous tubes with a minimum of risk or error and is particularly useful where a patient in surgery or intensive care must be supplied with a number of intravenous solutions. Pursuant to the embodiment of the invention illustrated in FIGS. 1 and 2, the clamping components are attached to base or frame 50. Accordingly, in use, the entire assembly is disposed proximately to a patient, for example, on a wall or stand. Subsequently, intravenous tubes are inserted between legs 14 and 16 of respective clamping members 12. Slider members 18 are shifted respective distances along the U-shaped clamping members 12 to squeeze the intravenous tubes and restrict flow to a determinable degree.

In an alternative embodiment of the invention illustrated in FIGS. 9–12, an intravenous flow regulating or delivery assembly comprises a plurality of intravenous flow regulators 80 each including a generally U-shaped clamp 82 having two legs 84 and 86 connected to one another by a bight portion 88. At a free end, at least one leg 84 is provided with a plurality of serrations or teeth 90 for engaging an intravenous tube 92 and squeezing the tube to controllably restrict fluid flow therethrough. One or both legs 84 and 86 are additionally provided along one edge (see FIG. 11) with a respective retaining tooth 94 and 96 for enhancing the attachment of tube 92 to clamp 82, i.e., for retaining the tube between legs 84 and 86 during use of the device. Also for retention or attachment purposes, bight portion 88 is formed with a notch 98 which receives tube 92 without affecting the cross-sectional area of the tube lumen.

Figure 12:
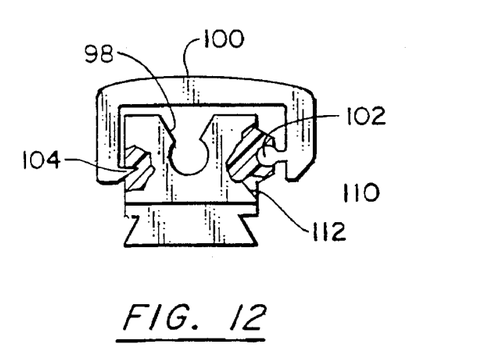
FIG. 12 is a schematic end elevational view, partially broken away, of the intravenous clamping and flow regulating device of FIGS. 9–11.

As shown in FIG. 12, a U-shaped slider member 100 is provided with a cylindrical lug 102 which is slidingly received in a cylindrical slot (not designated) in leg 86. On another side, slider member 100 is formed with an inwardly projecting detent 104 which is slidingly received in a snap-lock fit in a groove 106 (FIGS. 10 and 11) provided along an outwardly facing surface 108 of leg 84. In a region about lug 102, slider member 100 has a shoulder 110 which serves arrest function, limiting the angle taken by the slider member upon a rotation thereof about lug 102. Upon an outward rotation of slider member 100, preparatory to a removal or insertion of intravenous tube 92 between legs 84 and 86, shoulder 110 enters a recess 112 provided in leg 86.

Figure 10:
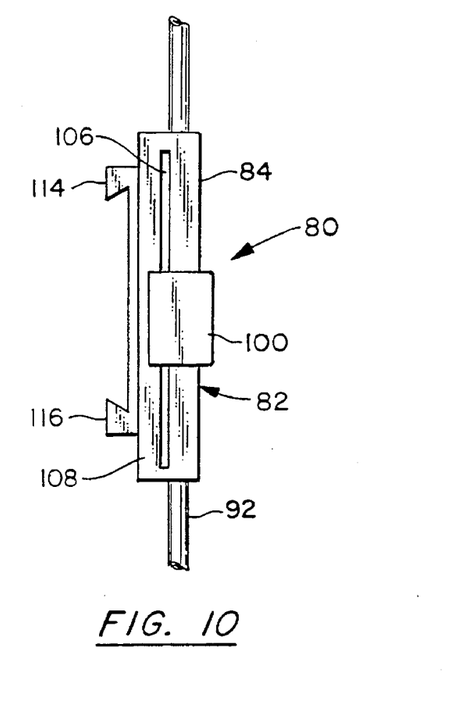
FIG. 10 is a schematic side elevational view, on a larger scale, of the intravenous clamping and flow regulating device of FIG. 9.
Figure 11:
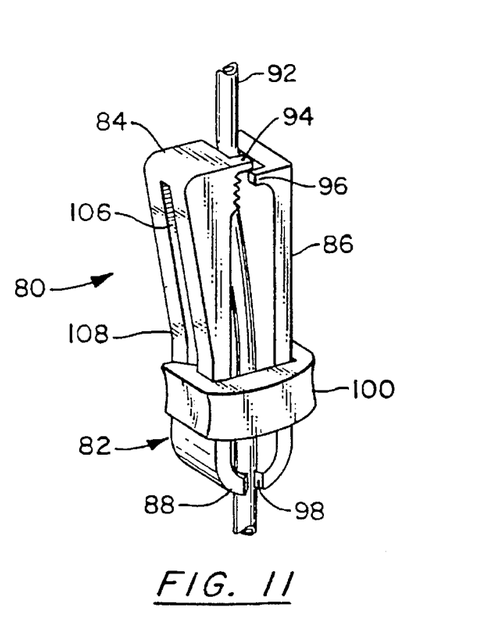
FIG. 11 is a schematic perspective view of the intravenous clamping and flow regulating device of FIGS. 9 and 10.
Figure 13:
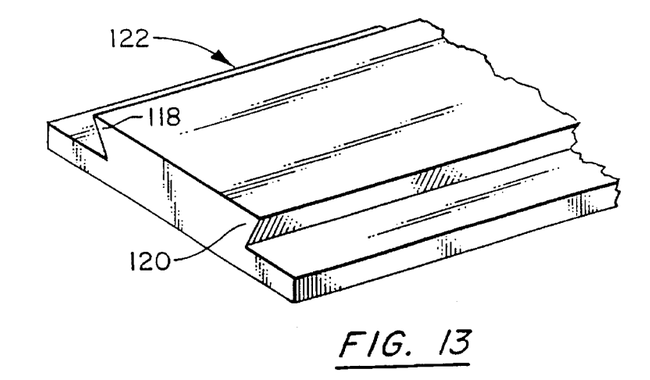
FIG. 13 is a partial perspective view of a frame member or holder for the clamping device of FIGS. 9–12.

As further illustrated particularly in FIG. 10, flow regulating device 80 is provided with a pair of dovetailed connectors 114 and 116 affixed to leg 86 for cooperating with respective dovetailed edges 118 and 120 on a frame or bracket 122, shown in FIG. 13. Frame 122 is attached to a wall or to a stand, above a patient, or to an infusion apparatus such as a dialysis machine, etc., and holds virtually any number of flow regulators 80. Frame 122 serves as a work station for the ordering and arranging of multiple intravenous flow regulators.

Generally, it is contemplated that flow regulators 80 are slidingly attached to frame 122 upon a disposition thereof near a patient. Subsequently, respective intravenous tubes 92 are inserted between the legs 84 and 86 of clamps 82. It is also possible, however, for tubes 92 to be attached first to flow regulators 80, prior to the mounting thereof to frame 122.

Figure 14:
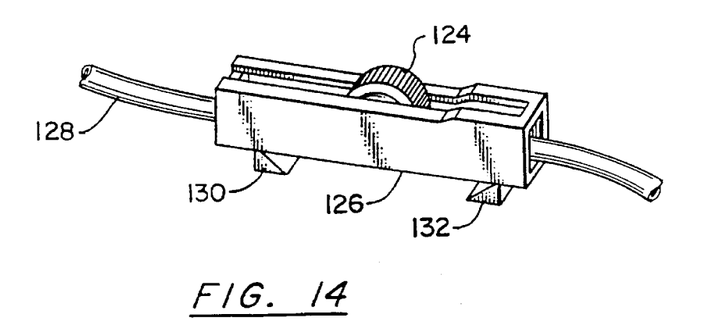
FIG. 14 is a perspective view of another intravenous flow regulating device removably attachable to the frame or holder of FIG. 13.

It is to be noted that other types of IV flow regulators may be attached to frame 122. FIG. 14 illustrates an IV flow regulator with a roller 124 mounted to a holder 126. To varying degrees, depending on the desired flow rate, roller 124 presses an IV tube 128 which passes through holder 126. Dovetailed connectors 130 and 132 on holder 126 cooperate with respective dovetailed edges 118 and 120 on work station frame or bracket 122 to attach the regulator to the frame.

Figure 15:
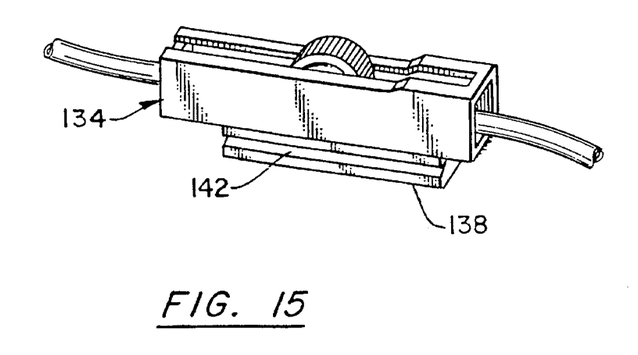
FIG. 15 is perspective view of another intravenous flow regulating device.
Figure 16:
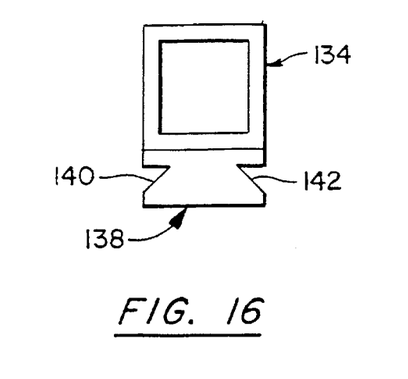
FIG. 16 is a schematic transverse cross-sectional view of the intravenous flow regulating device of FIG. 15.
Figure 17:
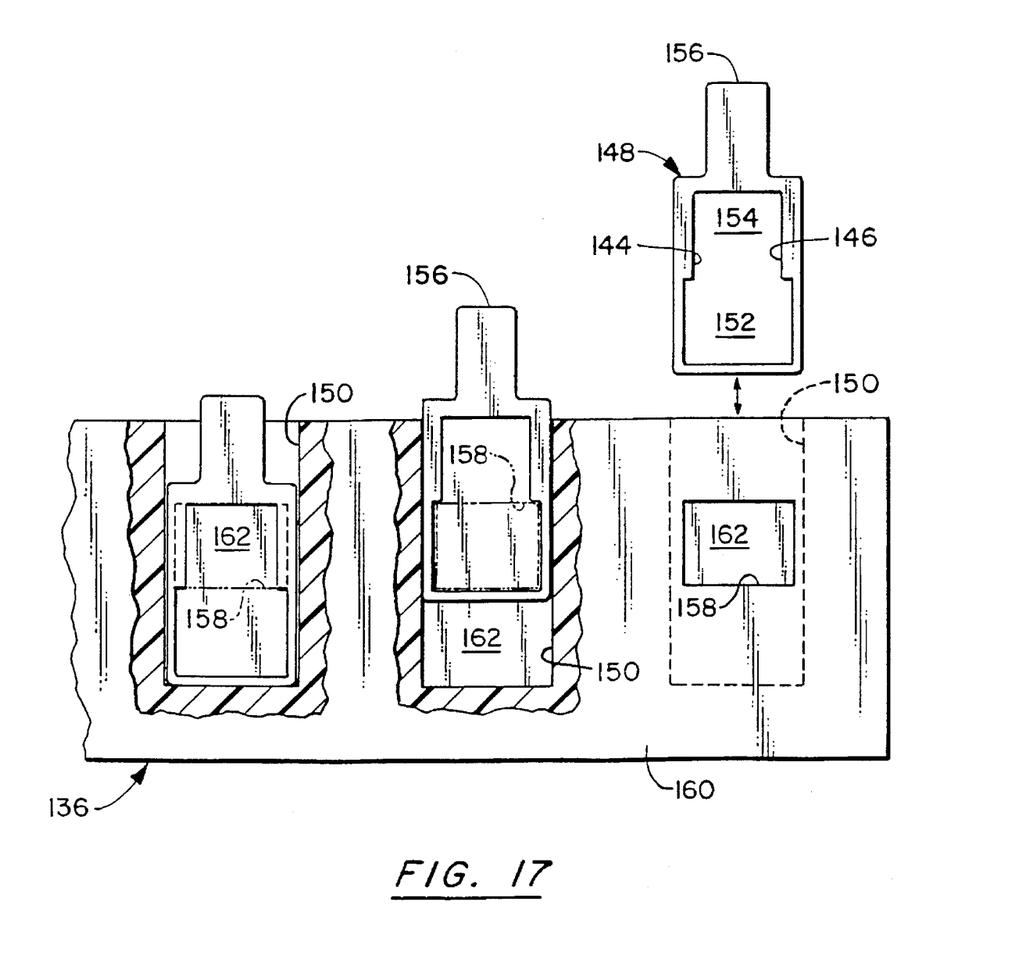
FIG. 17 is a schematic partial elevational view of a work station frame or bracket assembly for holding the device of FIG. 15.

As depicted in FIGS. 15–17, other structures are possible for releasably attaching an IV flow regulator/clamp 134 to a work station bracket 136. Regulator 134 is provided in a base part 138 with longitudinally extending grooves or keyways 140 and 142 (FIGS. 15 and 16). Grooves or keyways 140 and 142 slidingly receive inwardly facing edges 144 and 146 of a planar locking member 148 (FIG. 17). FIG. 17 shows a plurality of such locking members 148 inserted to different degrees in respective flat slots 150 in bracket 136. Each locking member 148 is provided with an opening having a large portion 152 and a smaller portion 154. Edges 144 and 146 define sides of smaller opening portion 154.

To attach flow regulator 134 to work station bracket 136, the user grasps a tab 156 on a selected locking member 148 and slides that locking member so that its large opening portion 152 is aligned with an aperture 158 in a front face or wall 160 of bracket 136. Base part 138 is then inserted through aperture 158 and large opening portion 152 to engage a rear wall 160 of bracket 136. Then locking member 148 is pushed into the respective slot 150 so that smaller opening portion 154 is aligned with aperture 158 and so that edges 144 and 146 are inserted into keyways 140 and 142, thereby locking the IV flow regulator 134 to bracket 136. Removal of the IV flow regulator from the bracket proceeds by reversing these steps.

Figures 18, 19, 20, 21, 22, 23, 24, 25:
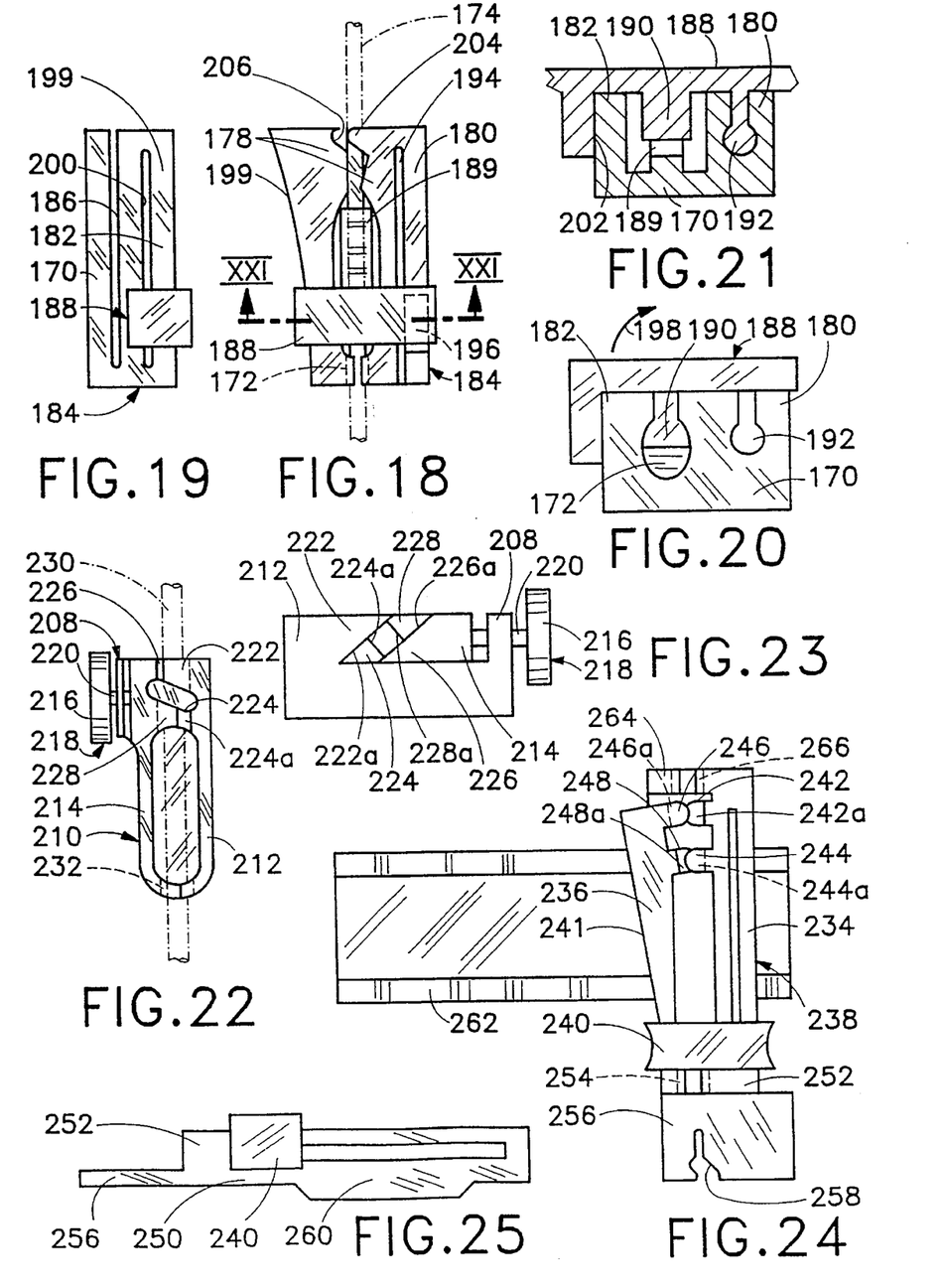
FIG. 18 is top or plan view of an intravenous flow regulator or clamping device in accordance with the present invention.
FIG. 19 is a side elevational view of the regulator or device of FIG. 18.
FIG. 20 is an end elevational view of the regulator or device of FIGS. 18 and 19.
FIG. 21 is a transverse cross-sectional view taken along line XXI—XXI in FIG. 18.
FIG. 22 is a top or plan view of another intravenous flow regulator or clamping device in accordance with the present invention.
FIG. 23 is an end elevational view of the intravenous flow regulator or clamping device of FIG. 22.
FIG. 24 is a top or plan view of a further intravenous flow regulator or clamping device in accordance with the present invention.
FIG. 25 is a side elevational view of the intravenous flow regulator or clamping device of FIG. 24.

As illustrated in FIGS. 19–21, an intravenous flow regulator or clamping device comprises a base or frame body 170 which is provided at one end with a notch 172 for attaching an intravenous tube 174 to the frame body. Intravenous tube 174 is inserted into notch 172 and through a pair of jaws 178 at an end of the frame body 170 opposite notch 172. Jaws 178 are located on legs or rails 180 and 182 of a U-shaped clamping member 184 attached to frame body 170. One leg 180 is rigid or integral with frame body 170, while the other leg 182 is movable alternately towards and away from leg 180 in opposition to an internal spring force of leg 182. Leg 182 is separated along its length from frame body 170 by a slot 186 (FIG. 19).

U-shaped clamping member 184, particularly including jaws 178, is a first pressure application component of the intravenous flow regulator or clamping device. A U-shaped slider or actuator member 188 is slidably attached to legs 180 and 182 of U-shaped clamping member 184 for pressing leg 182 towards leg 180 and alternately releasing leg 182 to vary the flow cross-section of intravenous tube 174. The closer leg 182 is to leg 180, the smaller the flow cross-section of intravenous tube 174 and consequently the lower the flow rate along the flow path defined by the intravenous tube.

Another pressure applicator disposed on frame body 170 includes an inclined surface or ramp 189 which cooperates with a projection 190 on slider member 188 to squeeze or compress intravenous tube 174 in a direction perpendicular to the plane of the drawing. Jaws 178 compress intravenous tube 174 in a direction in the plane of the drawing. This compression of intravenous tube 174 at two points relatively closely spaced along the flow path results in a twisting of the intravenous tube. Compared with traditional clamps, this twisting militates against inadvertent shifting of the intravenous tube and concomitant unintentional changes in the flow rate. Thus, the clamping of intravenous tube 174 in two substantially different directions serves to increase the reliability of intravenous flow regulation.

Slider member 188 includes a cylindrical axial pin 192 which is disposed in a longitudinally extending groove 194 in leg or rail 182. Leg 182 is provided at one end with a cutout 196 (FIG. 18) for enabling a pivoting of slider member 188 about groove 194, as indicated by an arrow 198, thereby providing an opening for the insertion or removal of intravenous tube 174 from the device.

Leg or rail 182 is provided along an outer camming surface 199 with a groove 200 (FIG. 19) for receiving a tooth 202 (FIG. 21) on slider member 188 in a snap-lock fit to releasably lock slider member 188 to U-shaped clamping member 184. In addition, one of the jaws 178 is provided with a finger 204 which fits into a recess 206 on the other jaw. Finger 204 serves to hold intravenous tube 174 between jaws 178 during use of the device.

As illustrated in FIGS. 22 and 23, another intravenous flow regulator or clamping device comprises a frame body 208 incorporating a U-shaped clamping member 210. Clamping member 210 in turn includes a first leg or rail 212 rigid with frame body 208 and another leg or rail 214 laterally movable alternately towards and away from leg 212 in response to the turning of a wheel 216 of a screw type actuator mechanism 218. Wheel 216 is connected to a threaded shaft 220 which is rotatably connected to frame body 208 and which has a free end in engagement with leg or rail 214.

Legs 212 and 214 are each provided at one end with a pair of wedge-shaped projections 222, 224 and 226, 228. Projections 222 and 226 are opposed to one another to function as a first pressure applicator and have inclined clamping surfaces 222a and 226a which extend in parallel planes at all times. Similarly, projections 224 and 228 are opposed to one another to function as a second pressure applicator and have inclined clamping surfaces 224a and 228a which also extend in parallel planes. The planes of surfaces 222a and 226a are oriented at a substantial angle (e.g., 60°, 90°) relative to the planes of surfaces 224a and 228a. In other words, the common angle of inclination of surfaces 222a and 226a is substantially staggered relative to the common angle of inclination of surfaces 224a and 228a.

Leg 214 functions like a movable carrier for wedge-shaped projections 226, 228. In response to the turning of wheel 216 in one direction, leg 214 moves, in opposition to an internal spring force, towards leg 212. Concomitantly, wedges 222 and 224 move towards wedges 226 and 228. An intravenous tube 230 inserted in a gap (not designated) between surfaces 222a and 226a and a gap (not designated) between surfaces 224a and 228a is squeezed or compressed, whereby a flow cross-section of the tube is decreased to controllably vary flow rate.

It is to be noted that because the planes of surfaces 222a and 226a are oriented at a substantial angle relative to the planes of surfaces 224a and 228a, the intravenous flow regulator or clamping device effectuates a twisting of intravenous tube 230. As pointed out above, this twisting prevents or reduces inadvertant shifting of the intravenous tube and concomitant unintentional changes in the flow rate.

Frame body 208 is provided at one end with a notch 232 for attaching intravenous tube 230 to the intravenous flow regulator or clamping device.

FIGS. 24 and 25 depict an intravenous flow regulator or clamping device similar to that of FIGS. 22 and 23, except that the relative shifting of legs or rails 234 and 236 of a U-shaped clamping member 238 is implemented via a slider type actuator member 240 slidably secured to legs 234 and 236, as described hereinabove with reference to FIGS. 18–21. Slider member 240 cooperates in a camming action with an outer surface 241 of leg 236 to shift that leg laterally.

As further depicted in FIGS. 24 and 25, legs 234 and 236 are provided along opposed inner faces with pair of wedge-shaped clamping projections 242, 244 and 246, 248. Projections 242 and 246 are opposed to one another and have inclined clamping surfaces 242a and 246a which extend in parallel planes at all times. Similarly, projections 244 and 248 are opposed to one another and have inclined clamping surfaces 244a and 248a which also extend in parallel planes to function as a second pressure applicator. The planes of surfaces 242a and 246a are oriented at a substantial angle (e.g., 60°, 90°) relative to the planes of surfaces 244a and 248a. In other words, the common angle of inclination of surfaces 242a and 246a is substantially staggered relative to the common angle of inclination of surfaces 244a and 248a.

Leg 236 functions like a movable carrier for wedge-shaped projections 246, 248. In response to the sliding of member 240 in one direction, leg 236 moves, in opposition to an internal spring bias, towards leg 234. Concomitantly, wedges 246 and 248 move towards wedges 242 and 244. An intravenous tube (not shown) inserted in a gap (not designated) between surfaces 242a and 246a and a gap (not designated) between surfaces 244a and 248a is compressed to vary a flow cross-section of the tube to control flow rate. Because the planes of surfaces 242a and 246a are oriented at a substantial angle relative to the planes of surfaces 244a and 248a, the intravenous flow regulator or clamping device effectuates a twisting of an intravenous tube (not shown) with advantages as noted above.

U-shaped clamping member 238 is attached to a base or frame body 250 (FIG. 25). Legs 234 and 236 of U-shaped clamping member 238 are connected to one another by a bight portion 252 which has a notch 254 for attaching an intravenous tube (not shown) to the intravenous flow regulator or clamping device. In addition, frame body 250 has an extension plate 256 which is provided with an ancillary notch 258 for additionally securing the intravenous tube to the intravenous flow regulator or clamping device.

As further illustrated in FIGS. 24 and 25, frame body 250 is provided with a dove-tailed connector 260 for slidably and releasably securing the intravenous flow regulator or clamping device to a work station holder or bracket 262, as described hereinabove with reference to FIG. 13 et seq. It is to be noted that virtually any of the intravenous flow regulators or clamping devices described herein may be incorporated into larger assemblies or work stations by such connectors and brackets. The connectors or brackets may be attached directly to infusion apparatus, e.g., dialysis machines, OR oxygenation machines, etc. The brackets may take different forms such as semi-cylindrical sections or multiple ribs arranged in a cylindrical array (as in a cylindrical section provided with grooves).

As additionally illustrated in FIG. 24, frame body 250 is provided at an end opposite bight portion 252 with a transversely extending flange 264 formed with a notch 266 which also serves for attaching an intravenous tube to the intravenous flow regulator or clamping device. Slider-type actuator member 240 is attached to U-shaped clamping member 238 and hence to frame body 250 in a manner similar to that described above, for instance, with respect to FIGS. 18–21.

Figures 26, 27, 28, 29, 30, 31, 32, 33:
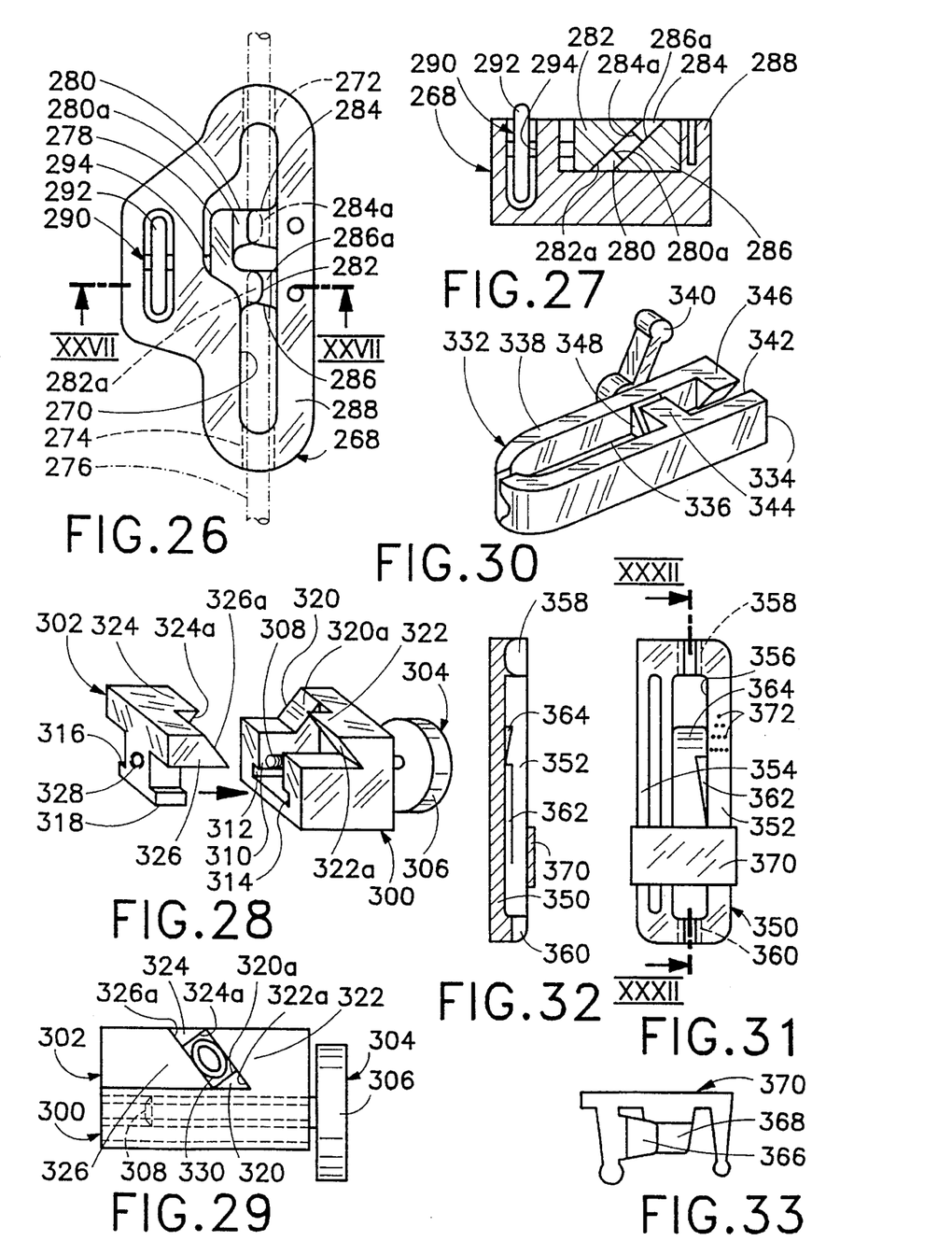
FIG. 26 is a top or plan view of an additional intravenous flow regulator or clamping device in accordance with the present invention.
FIG. 27 is a transverse cross-sectional view taken along line XXVII—XXVII in FIG. 26.
FIG. 28 is a schematic exploded perspective view of yet another intravenous flow regulator or clamping device in accordance with the present invention.
FIG. 29 is a schematic end elevational view of the intravenous flow regulator or clamping device of FIG. 28.
FIG. 30 is a schematic perspective view of yet a further intravenous flow regulator or clamping device in accordance with the present invention.
FIG. 31 is a top or plan view of yet another intravenous flow regulator or clamping device in accordance with the present invention.
FIG. 32 is a longitudinal cross-sectional view taken along line XXXII—XXXII in FIG. 31.
FIG. 33 is an elevational view of a slider member of the intravenous flow regulator or clamping device of FIGS. 31 and 32.

As depicted in FIGS. 26 and 27, another intravenous flow regulator or clamping device comprises a substantially rigid oval shaped frame body 268 provided with an elongate recess 270 and, at opposite ends of the recess, with a pair of notches 272 and 274 for receiving an intravenous tube 276 in a snap-lock kind of fit. A movable carrier 278 is mounted to frame body 268 inside recess 270. On one side carrier 278 is provided with a pair of inwardly projecting, oppositely inclined, pressure applying wedges 280 and 282. Wedges 280 and 282 have clamping surfaces 280a and 282a which are parallel to corresponding clamping surfaces 284a and 286a of pressure applicator wedges 284 and 286 attached to a side wall 288 of recess 270. Carrier 278 and, accordingly, wedges 280 and 282 with their clamping surfaces 280a and 282a are shifted laterally towards and away from wedges 284 and 286 by means of a screw-type actuator mechanism 290. Mechanism 290 includes a wheel 292 rotatably mounted to frame body 268 and a threaded shaft 294 rotatably secured at one end to carrier 278.

Clamping surfaces 280a and 282a of wedges 280 and 282 and clamping surfaces 284a and 286a of wedges 284 and 286 define therebetween respective gaps which receive intravenous tube 276. Tube 276 is inserted into those gaps when carrier 278 is in a withdrawn or retracted position relative to wedges 284 and 286 and side wall 288. At that time, the gaps have a relately large breadth.

Clamping surfaces 280a and 284a are oriented at a substantial angle (60°, 90°, etc.) to clamping surfaces 282a and 286a so that tube 276 is twisted upon a shifting of carrier 278 and wedges 280 and 282 towards wedges 284 and 286. This twisting enhances the connection of tube 276 to the intravenous flow regulator or clamping device and reduces, if not eliminates, inadvertant changes in intravenous flow rate owing to tugging on the intravenous tube.

As illustrated in FIGS. 28 and 29, yet another intravenous flow regulator or clamping device operating in accordance with above-defined principles comprises two cooperating clamping components 300 and 302. The one component 300 has a screw-type actuator mechanism 304 including a rotary knob or wheel 306 and a threaded shaft or spindle 308. Spindle 308 extends into a trackway 310 which is provided with a pair of longitudinal slots 312 and 314 for receiving guide wings or flanges 316 and 318 on component 302.

Component 300 is formed with a pair of wedge-shaped portions 320 and 322 having oppositely inclined clamping surfaces 320a and 322a. Similarly, component 302 is formed with a pair of wedge-shaped portions 324 and 326 having oppositely inclined clamping surfaces 324a and 326a. Surfaces 320a and 324a are disposed in parallel planes which extend at a substantial angle relative to planes of parallel coacting surfaces 322a and 326a.

Component 302 is provided with an internally threaded bore 328 for receiving spindle 308. A turning of knob 306 thus shifts components 300 and 302, and concomitantly surfaces 320a, 322a and 324a, 326a, alternately towards and away from one another to vary a flow cross-section of an intravenous tube 330 inserted into gaps defined by surfaces 320a and 324a and by surfaces 324a and 326a.

A further intravenous flow regulator or clamping device functioning pursuant to afore-described principles of operation is illustrated in FIG. 30. A U-shaped clamping member 332 includes a first leg or rail 334 integral with or fixed to a frame body 336 and a second leg or rail 338 which is movable laterally relative to leg 334 in opposition to an internal spring bias of the leg 338. Motion of leg 338 is implemented by a camming actuator lever 340. Legs 334 and 338 are provided with oppositely inclined clamping wedges 342, 344 and 346, 348, which function as described above with respect to the embodiments of FIGS. 22, 24, 26, and 28. Leg 338 functions like a movable carrier for wedges 346 and 348.

As depicted in FIGS. 31–33, yet a further intravenous flow regulator or clamping device functioning according to the principles described above includes an elongate frame body or base 350 provided with a pair of parallel rails 352 and 354 disposed on opposite sides of a recess 356. Frame body 350 is formed with a pair of notches 358 and 360 for attaching an intravenous tube (not shown) to the intravenous flow regulator or clamping device. Inside recess 356 are disposed a pair of ramps or surfaces 362 and 364 inclined in respective planes oriented at 90° relative to one another. Inclined surfaces 362 and 364 are paired with respective projections or pressure surfaces 366 and 368 on a slider type actuator member 370. Member 370 is slidably attached to rails 352 and 354 for motion therealong under the control of an operator or user.

During use of the intravenous flow regulator or clamping device of FIGS. 31–33, inclined surfaces 362 and 364 and projections 366 and 368 cooperate with one another to compress an intravenous tube inserted in recess 356, thereby varying the flow rate of intravenous fluid through the tube. Inclined surfaces 362 and 364 and likewise pressure projections 366 and 368 are staggered with respect to one another so that an intravenous tube inserted in recess 356 is simultaneously constricted and twisted upon a shifting of slider member 370 from notch 358 towards notch 360.

Rail 352 or 354 is provided with a series of markings 372, e.g., dots of increasing number, to designate the flow rate of the intravenous tube depending on the position of slider member 370. Similar markings may be provided on legs or rails of U-shaped clamping members and/or on knobs or wheels of screw-type actuator mechanisms described hereinabove.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A flow regulator device for intravenous tubing, comprising:

a frame body;

means on said frame body for attaching a flexible tube to said frame body;

first pressure application means including a first clamping surface and a second clamping surface movable relative to one another, disposed on said frame body and engageable with said tube for alternately compressing and releasing said tube along a first line of action in a first plane;

second pressure application means, disposed on said frame body spaced from said first pressure application means along a flow path of said tube and engageable with said tube, for alternately compressing and releasing said tube along a second line of action in a second plane, said second line of action being oriented at a substantial angle with respect to said first line of action, said second plane being spaced from said first plane along the flow path of said tube, said second pressure application means including a third clamping surface and a fourth clamping surface movable relative to one another; and actuator means disposed on said frame and operatively connected to said first pressure application means and said second pressure application means for operating said first and second pressure application means to vary a fluid flow cross-section in said tube to enable a steady fluid flow through said tube at any of a plurality of different positive feed rates.

2. The device defined in claim 1 wherein said first clamping surface and said second clamping surface extend at all times in substantially parallel planes, said third clamping surface and said fourth clamping surface being disposed at all times in substantially parallel planes, the planes of said first clamping surface and said second clamping surface being oriented at said angle relative to the planes of said third clamping surface and said fourth clamping surface, said first clamping surface and said second clamping surface defining therebetween a first gap, said third clamping surface and said fourth clamping surface defining therebetween a second gap, said first gap and said second gap being substantially aligned with one another so that said tube is insertable in said first gap between said first clamping surface and said second clamping surface and in said second gap between said third clamping surface and said fourth clamping surface, said actuator means including shifting means mounted to said frame body for shifting said first clamping surface and said second clamping surface alternately towards and away from one another and for shifting said third clamping surface and said fourth clamping surface alternately towards and away from one another to thereby vary a fluid flow cross-section in an tube inserted in said first gap between said first clamping surface and said second clamping surface and in said second gap between said third clamping surface and said fourth clamping surface.

3. The device defined in claim 2 wherein said first clamping surface and said third clamping surface are stationary with respect to said frame body, said second clamping surface and said fourth clamping surface being attached to a carrier member movably mounted to said frame body, said shifting means being operatively connected to said carrier member to shift said carrier member alternatively in opposite directions.

4. The device defined in claim 3 wherein said shifting means includes a screw mechanism.

5. The device defined in claim 3 wherein said shifting means includes a slider member, said carrier member including a spring biased element with a camming surface engaging said slider member.

6. The device defined in claim 5 wherein said spring biased element is a leg of a U-shaped clamping member incorporated into said frame body.

7. The device defined in claim 1 wherein said actuator means includes means for simultaneously operating said first pressure application means and said second pressure application means to vary a fluid flow cross-section in said tube.

8. The device defined in claim 7 wherein said actuator means includes a screw mechanism.

9. The device defined in claim 7 wherein said actuator means includes a slider member slidably mounted to said frame body, said frame body being provided with a spring biased element having a camming surface engaging said slider member.

10. The device defined in claim 7 wherein said actuator means includes a slider member slidably mounted to said frame body, said frame body being provided with a pair of inclined surfaces disposed in planes oriented at said angle relative to one another, said slider member being provided with a pair of pressure surfaces coacting respective ones of said inclined surfaces, said pressure surfaces being disposed in planes oriented at said angle relative to one another, said first pressure application means and said second pressure application means including respective ones of said pressure surfaces.

11. The device defined in claim 1 wherein said angle is approximately 90 degrees.

12. A flow regulator device for intravenous tubing, comprising:

a frame body;

means on said frame body for attaching a tube to said frame body; and two pairs of cooperating clamping surfaces disposed on said frame body and engageable with said tube at two positions longitudinally spaced from one another along said tube for variably compressing said tube at said two positions to vary a fluid flow cross-section in said tube to enable a steady fluid flow through said tube at ally of a plurality of different positive feed rates.

13. The device defined in claim 12 wherein a first pair of said clamping surfaces is engageable with said tube for alternately compressing and releasing said tube along a first line of action in a first plane;

a second pair of said clamping surfaces being engageable with said tube for alternately compressing and releasing said tube along a second line of action in a second plane, said second line of action being oriented at a substantial angle substantially greater than zero degrees and substantially less than 180 degrees with respect to said first line of action, said second plane being spaced from said first plane along the flow path of said tube; and actuator means disposed on said frame and operatively connected to said first pressure application means and said second pressure application means for operating said first and second pressure application means to vary a fluid flow cross-section in said tube.

14. A method for use in feeding medical treatment fluid to a patient, comprising the steps of:

providing a frame body;

attaching a flexible tube to said frame body; and upon attachment of said tube to said frame body, operating pressure application componentry on said frame body to compress said tube along a first line of action in a first plane and simultaneously compress said tube along a second line of action in a second plane to thereby vary a fluid flow cross-section in said tube, said second line of action being oriented at an angle substantially greater than zero degrees and substantially less than 180 degrees with respect to said first line of action and said second plane being spaced from said first plane along a flow path of said tube, whereby said tube is twisted during said steps of compressing.

15. The method defined in claim 14 wherein said step of operating includes the step of moving a first clamping surface and a second clamping surface relatively towards one another along said first line of action and further includes the step of moving a third clamping surface and a fourth clamping surface relatively towards one another along said second line of action.

16. The method defined in claim 15 wherein said steps of moving include the steps of maintaining said first clamping surface and said second clamping surface substantially parallel to one another and maintaining said third clamping surface and said fourth clamping surface substantially parallel to one another.

17. The method defined in claim 16 wherein said first clamping surface and said second clamping surface define therebetween a first gap and said third clamping surface and said fourth clamping surface define therebetween a second gap substantially aligned with said first gap, said step of attaching including the step of inserting said tube into said first gap and said second gap.

18. The method defined in claim 15 wherein said first clamping surface and said third clamping surface are fixed relative to said frame body, said second clamping surface and said fourth clamping surface being formed on a spring biased element movable relative to said frame body, said step of moving including the step of sliding a slider member along said spring biased element to push said spring biased element towards said first clamping surface and said third clamping surface.

19. The method defined in claim 15 wherein said first clamping surface and said third clamping surface are fixed relative to said frame body, said second clamping surface and said fourth clamping surface being formed on a carrier member, said step of moving including the step of operating a screw mechanism operatively coupled to said spring element.

20. A flow regulator device for intravenous tubing, comprising:

a frame body provided with a guide rail fixed to said frame, said frame body being further provided with an additional rail having an elongate camming surface, said additional rail being movably connected to said frame body; and shifting means, including a slider member slidably mounted to said frame body for motion along an essentially linear path in camming action engagement with said elongate camming surface, for shifting said additions rail relative to said guide rail during motion of said slider member along said path and for concomitantly changing a distance between said guide rail and said additional rail to thereby alternately compress and release and concomitantly vary a fluid flow cross-section in a flexible tube inserted between said guide rail and said additional rail, said elongate camming surface extending along said path and being inclined relative thereto.

21. The device defined in claim 20 wherein said additional rail moves in a first plane in response to sliding of said slider member along said guide rail, said elongate surface being inclined in a second plane oriented at a substantial angle with respect to said first plane.

22. The device defined in claim 21 wherein said angle is approximately 90 degrees.

23. The device defined in claim 20 wherein said guide rail and said additional rail are legs of a U-shaped clamping member incorporated into said frame body.

24. The device defined in claim 20, further comprising means on said frame body for maintaining said tube in a predetermined position between said guide rail and said additional rail.

25. The device defined in claim 24 wherein said means for maintaining includes a notch in said frame body for receiving said tube.

* * * * *